United States Patent [19]

Jautelat et al.

[11] Patent Number: 5,175,169
[45] Date of Patent: Dec. 29, 1992

[54] HALOGENOVINYL-AZOLE DERIVATIVES

[75] Inventors: Manfred Jautelat, Bursheid; Dieter Berg, Wuppertal; Stefan Dutzmann, Duesseldorf; Wilhelm Brandes, Leichlingen; Gerd Hänssler, Leverkusen; Astrid Mauler, Leichlingen; Wilfried Paulus, Krefeld; Monika Frie, Odenthal, all of Fed. Rep. of Germany

[73] Assignee: Bayer Aktiengesellschaft, Leverkusen, Fed. Rep. of Germany

[21] Appl. No.: 761,087

[22] Filed: Sep. 17, 1991

Related U.S. Application Data

[62] Division of Ser. No. 384,595, Jul. 24, 1989, Pat. No. 5,081,140.

Foreign Application Priority Data

Aug. 3, 1988 [DE] Fed. Rep. of Germany ....... 3826344
Feb. 22, 1989 [DE] Fed. Rep. of Germany ....... 3905377
Feb. 22, 1989 [DE] Fed. Rep. of Germany ....... 3905378

[51] Int. Cl.$^5$ .................. A01N 43/50; C07D 233/60
[52] U.S. Cl. .................................. 514/399; 514/184; 548/101; 548/341.1
[58] Field of Search ............... 548/101, 341; 514/184, 514/399

[56] References Cited

U.S. PATENT DOCUMENTS 4,927,833 5/1990 Kirby et al. ...................... 514/399

Primary Examiner—Patricia L. Morris
Attorney, Agent, or Firm—Sprung Horn Kramer & Woods

[57] ABSTRACT

New halogenovinyl-azole derivatives of the formula

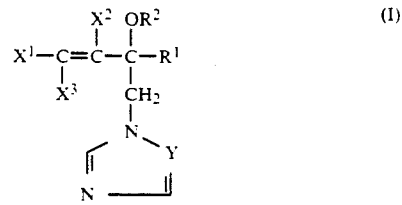

in which
$R^1$ represents optionally substituted alkyl, optionally substituted alkenyl, optionally substituted cycloalkyl or optionally substituted aryl, or represents optionally substituted heteroaryl,
$R^2$ represents hydrogen, alkyl, alkenyl, acyl or aralkyl
$X^1$ represents halogen,
$X^2$ represents halogen,
$X^3$ represents hydrogen or halogen
Y represents nitrogen or a CH group,
and acid addition salts and metal salt complexes thereof are very effective for combating microbes in plant protection and in the preservation of materials.

6 Claims, No Drawings

HALOGENOVINYL-AZOLE DERIVATIVES

This is a division of application Ser. No. 384,595 filed Jul. 24, 1989, now U.S. Pat. No. 5,081,140.

The present invention relates to new halogenovinyl-azole derivatives, several processes for their preparation and their use as microbicides in plant protection and in the preservation of materials.

It has already been disclosed that certain hydroxyethylazole derivatives containing an alkenyl group are suitable for combating fungi (compare EP-OS 0,207,590 and EP-OS 0,257,822). The action of these substances is good, but leaves something to be desired in some cases when low amounts are applied.

Further, it has already been disclosed that various azolyl derivatives can be used to preserve non-living organic substances against an attack by microorganisms (compare DE-OS (German Published Specification) 3,116,607). Thus, for example, 1-(4-chlorophenoxy)-3,3-dimethyl-1-(1,2,4-triazol-1-yl)-butan-2-ol and 1-(2,4-dichlorophenyl)-4,4-dimethyl-2-(1,2,4-triazol-1-yl)-pentan-3-ol can be used for the purpose mentioned above. The activity of these substances, however, is not always sufficient in the preservation of materials.

New halogenovinyl-azole derivatives of the formula

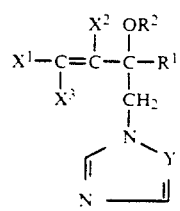

(I)

in which

R$^1$ represents optionally substituted alkyl, optionally substituted alkenyl, optionally substituted cycloalkyl or optionally substituted aryl, or represents optionally substituted heteroaryl, R$^2$ represents hydrogen, alkyl, alkenyl, acyl or aralkyl X$^1$ represents halogen, X$^2$ represents halogen, X$^3$ represents hydrogen or halogen Y represents nitrogen or a CH group, and acid addition salts and metal salt complexes thereof have now been found.

The compounds of the formula (I) contain an asymmetrically substituted carbon atom and can therefore be obtained in the two optical isomer forms. Depending on the position of the halogen atoms on the double bond, the substances of the formula (I) can additionally exist in two geometric isomer forms. The present invention relates both to the isomer mixtures and to the individual isomers.

It has furthermore been found that halogenovinyl-azole derivatives of the formula (I) and acid addition salts and metal salt complexes thereof are obtained by a process in which a) alkines of the formula

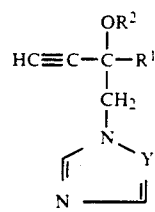

(II)

in which R$^1$, R$^2$ and Y have the abovementioned meaning, are reacted with halogen or compounds which supply halogen, in the presence of a diluent, or b) alkenes of the formula

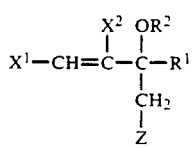

(III)

in which

R$^1$, R$^2$, X$^1$ and X$^2$ have the abovementioned meaning and

Z represents halogen, alkylsulphonate or arylsulphonate, are reacted with azoles of the formula

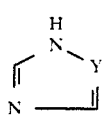

(IV)

in which Y has the abovementioned meaning, in the presence of an acid-binding agent and in the presence of a diluent, c) alkines of the formula

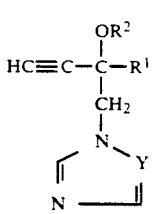

(II)

in which R$^1$, R$^2$ and Y have the abovementioned meaning, are reacted, in a first stage, with hypohalogenites of the formula

MOX$^4$  (V)

in which

M represents an alkali metal and

X$^4$ represents halogen, in the presence of a diluent, and in a second stage, the halogenoalkines thus obtained, of the formula

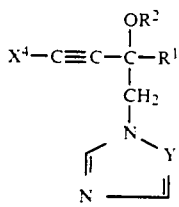

(VI)

in which $R^1$, $R^2$, $X^4$ and Y have the abovementioned meaning, are reacted with halogen or compounds which supply halogen, in the presence of a diluent and, if appropriate, an acid or a metal salt is then added onto the compounds of the formula (I) thus obtained.

Finally, it has been found that the new halogenovinyl-azole derivatives of the formula (I) and acid addition salts and metal salt complexes thereof have potent microbicidal properties and can be used in plant protection as well as in the preservation of materials.

Surprisingly, the substances according to the invention have a better fungicidal activity in plant protection than the already known compounds of the same type of action which have the greatest structural similarity.

Further, the compounds according to the invention are also surprisingly better suitable for combating undesired microorganisms in the preservation of materials than 1-(4-chlorophenoxy)-3,3-dimethyl-1-(1,2,4-triazol-1-yl)-butan-2-ol and 1-(2,4-dichlorophenyl)-4,4-dimethyl-2-(1,2,4-triazol-1-yl)-pentan-3-ol, which are structurally similar already known compounds of the same type of action.

Formula (I) provides a general definition of the halogeno-vinyl-azole derivatives according to the invention. Preferred compounds of the formula (I) are those in which $R^1$ represents straight-chain or branched alkyl having 1 to 6 carbon atoms, it being possible for each of these radicals to be substituted by one to three identical or different substituents from the group comprising halogen, cycloalkyl having 3 to 7 carbon atoms, phenyl and/or halogenophenyl, or $R^1$ represents alkenyl having 2 to 6 carbon atoms it being possible for each of these radicals to be substituted by one to three identical or different substituents from the group comprising halogen, phenyl and/or halogenophenyl, or $R^1$ represents cycloalkyl having 3 to 7 carbon atoms, it being possible for each of these cycloalkyl radicals to be substituted by one to three identical or different substituents from the group comprising halogen and/or alkyl having 1 to 4 carbon atoms, or $R^1$ represents phenyl, which can be substituted by one to three identical or different substituents from the group comprising halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy part, alkoximinoalkyl having 1 to 4 carbon atoms in the alkoxy part and 1 to 4 carbon atoms in the alkyl part, nitro and/or cyano, or $R^1$ represents an optionally benzo-fused five- or six-membered heteroaromatic radical having 1 to 3 heteroatoms, such as nitrogen, sulphur and/or oxygen, it being possible for each of these radicals to be substituted by one to three identical or different substituents from the group comprising halogen, alkyl having 1 to 4 carbon atoms, hydroxyalkyl having 1 to 4 carbon atoms, hydroxyalkinyl having 3 to 8 carbon atoms, alkoxy having 1 to 2 carbon atoms, alkylthio having 1 or 2 carbon atoms, halogenoalkyl, halogenoalkoxy and halogenoalkylthio having in each case 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy part, alkoximinoalkyl having 1 to 4 carbon atoms in the alkoxy part and 1 to 3 carbon atoms in the alkyl part, nitro and/or cyano, $R^2$ represents hydrogen, alkyl having 1 to 6 carbon atoms, alkenyl having 3 to 6 carbon atoms, acyl having 1 to 4 carbon atoms or phenylalkyl having 1 to 4 carbon atoms in the alkyl part, $X^1$ represents fluorine, chlorine, bromine or iodine, $X^2$ represents fluorine, chlorine, bromine or iodine, $X^3$ represents hydrogen, chlorine, bromine or iodine and Y represents a nitrogen atom or a CH group.

Particularly preferred compounds of the formula (I) are those in which $R^1$ represents methyl, ethyl, n-propyl, isopropyl, n-butyl, tert.-butyl, tert.-pentyl, 1-ethyl-1-methyl-propyl, 1,1-dimethyl-pentyl, 1,1,2-trimethylpropyl or 1,1-dimethyl-prop-2-enyl, it being possible for each of these abovementioned radicals to be substituted by one to three identical or different substituents from the group comprising fluorine, chlorine, bromine, phenyl, chlorophenyl, dichlorophenyl, fluorophenyl and/or difluorophenyl, or $R^1$ represents 1-methyl-cyclohexyl, cyclohexyl, 1-chloro-cyclopropyl, 1-methyl-cyclopropyl, cyclopropyl, 1-methyl-cyclopentyl, cyclopentyl or 1-ethyl-cyclopentyl, or represents phenyl, which can be substituted by one to three identical or different substituents from the group comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorofluoromethylthio, methoxycarbonyl, ethoxycarbonyl, methoximinoethyl, 1-methoximinoethyl, nitro and/or cyano, or $R^1$ represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be substituted by one to three identical or different substituents from the group comprising fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximino-ethyl, nitro, cyano, formyl, dimethoxymethyl, acetyl and/or propionyl, $R^2$ represents hydrogen, methyl, ethyl, n-propyl, isopropyl, n-butyl, allyl, formyl, acetyl, benzyl or phenethyl, $X^1$ represents fluorine, chlorine, bromine or iodine, $X^2$ represents fluorine, chlorine, bromine or iodine, and $X^3$ represents hydrogen, chlorine, bromine or iodine, and Y represents a nitrogen atom or a CH group.

Addition products of acids and those halogenovinyl-azole derivatives of the formula (I) in which $R^1$, $R^2$, $X^1$, $X^2$, $X^3$ and Y have those meanings which have been mentioned as preferred for these substituents are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluenesulphonic acid and 1,5-naphthalenedisulphonic acid.

Addition products of salts of metals of main groups II to IV and of sub-groups I and II and IV to VIII of the periodic table of the elements and those halogenovinyl-azole derivatives of the formula (I) in which $R^1$, $R^2$, $X^1$, $X^2$, $X^3$ and Y have those meanings which have been mentioned as preferred for these substituents are furthermore preferred compounds according to the invention.

Salts of copper, zinc, manganese, magnesium, tin, iron and nickel are particularly preferred here. Possible anions of these salts are those which are derived from those acids which lead to physiologically tolerated addition products. Particularly preferred acids of this type in this context are the hydrogen halide acids, such as, for example, hydrochloric acid and hydrobromic acid, and furthermore phosphoric acid, nitric acid and sulphuric acid.

Examples of suitable substances according to the invention are the halogenovinyl-azole derivatives listed in the following table.

TABLE 1

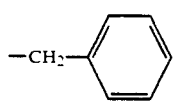

| $X^1$ | $X^2$ | $X^3$ | $R^1$ | $R^2$ | Y |
|---|---|---|---|---|---|
| I | I | H | —C(CH₃)₃ | H | N |
| F | F | H | —C(CH₃)₃ | H | N |
| I | I | H | —C(CH₃)₃ | H | CH |
| F | F | H | —C(CH₃)₃ | H | CH |
| Cl | Cl | H | —C(CH₃)₃ | CH₃ | N |
| Cl | Cl | H | —C(CH₃)₃ | C₂H₅ | N |
| Br | Br | H | —C(CH₃)₃ | —CH₂—C₆H₅ | N |
| Cl | Cl | H | —C(CH₃)₃ | —CH₂—C₆H₅ | N |
| Cl | Cl | H | —C(CH₃)(CH₃)—CH(CH₃)₂ | H | N |
| Cl | Cl | H | —C(CH₃)(CH₃)—C₂H₅ | H | N |
| Cl | Cl | H | —C(CH₃)(CH₃)—CH(CH₃)₂ | H | N |
| Cl | Cl | H | —C(CH₃)(CH₃)—CH=CH₂ | H | N |

TABLE 1-continued
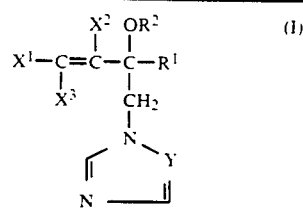
| X¹ | X² | X³ | R¹ | R² | Y |
|----|----|----|----|----|---|
| Cl | Cl | H | cyclohexyl-C(CH₃)< | H | N |
| Cl | Cl | H | cyclopentyl-C(CH₃)< | H | N |
| Cl | Cl | H | cyclopentyl-C(C₂H₅)< | H | N |
| Cl | Cl | H | -C(CH₃)(CH₃)-C₆H₅ | H | N |
| Cl | Cl | H | -C(CH₃)(CH₃)-CH₂F | H | N |
| Cl | Cl | H | -C(CH₂F)(CH₃)-CH₂F | H | N |
| Cl | Cl | H | -C(CH₃)(CH₃)-CH₂Cl | H | N |
| Cl | Cl | H | -C(CH₃)(CH₃)-CH=CH-Cl | H | N |
| Cl | Cl | H | -C(CH₂Cl)(CH₃)-CH₂Cl | H | N |
| Cl | Cl | H | -C(CH₃)(CH₃)-C₆H₄-Cl (4-Cl) | H | N |
| Cl | Cl | H | -C(CH₃)(CH₃)-C₆H₃-Cl₂ (2,4-Cl) | H | N |

TABLE 1-continued
$$\underset{X^3}{\overset{X^1}{\phantom{X}}}C=C\underset{\underset{\underset{N\overset{\phantom{X}}{=}}{\overset{\phantom{X}}{\underset{CH_2}{|}}}}{\overset{X^2}{|}}}{\overset{\phantom{X}}{|}}\underset{\underset{N-Y}{|}}{\overset{OR^2}{\overset{|}{C}}}R^1 \qquad (I)$$
| X¹ | X² | X³ | R¹ | R² | Y |
|----|----|----|----|----|---|
| Cl | Cl | H | 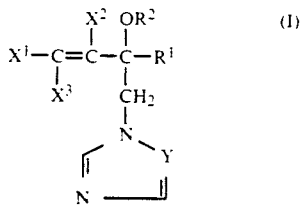 | H | N |
| Cl | Cl | H | 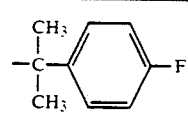 | H | N |
| Cl | Cl | H | 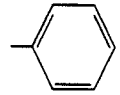 | H | N |
| Cl | Cl | H | 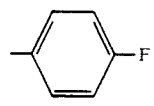 | H | N |
| Cl | Cl | H | 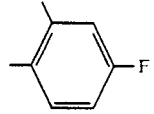 | H | N |
| Cl | Cl | H | 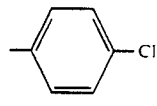 | H | N |
| Cl | Cl | H | 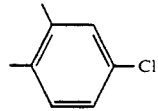 | H | N |
| Cl | Cl | H | 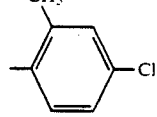 | H | N |
| Cl | Cl | H | 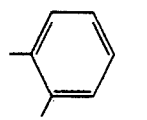 | H | N |
| Cl | Cl | H | 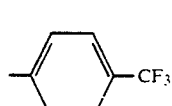 | H | N |

TABLE 1-continued $$X^1-C=C-C-R^1 \quad (I)$$
with $X^2$, $OR^2$ on the middle carbon, $X^3$ on the first carbon, and $CH_2-N$ (imidazole/triazole with Y) below.

| $X^1$ | $X^2$ | $X^3$ | $R^1$ | $R^2$ | Y |
|---|---|---|---|---|---|
| Cl | Cl | H | 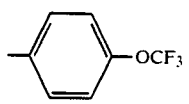 4-OCF₃-phenyl | H | N |
| Cl | Cl | H | 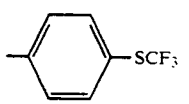 4-SCF₃-phenyl | H | N |
| Cl | Cl | H | 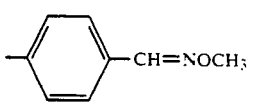 4-CH=NOCH₃-phenyl | H | N |
| Cl | Cl | H | 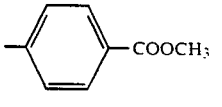 4-COOCH₃-phenyl | H | N |
| Cl | Cl | H | 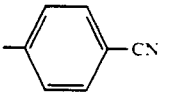 4-CN-phenyl | H | N |
| Cl | Cl | H | 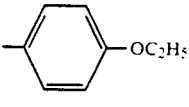 4-OC₂H₅-phenyl | H | N |
| Cl | Cl | H | 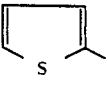 2-thienyl | H | N |
| Cl | Cl | H | 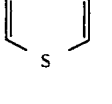 3-thienyl | H | N |
| Cl | Cl | H | 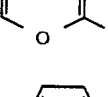 2-furyl | H | N |
| Cl | Cl | H | 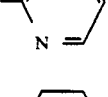 2-pyridyl | H | N |
| Cl | Cl | H | 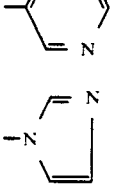 3-pyridyl | H | N |
| Cl | Cl | H |  imidazolyl | H | N |

TABLE 1-continued $$X^1-C(X^3)=C(X^2)-C(OR^2)(R^1)(CH_2-N(-N=Y-CH=CH-)) \quad (1)$$

| $X^1$ | $X^2$ | $X^3$ | $R^1$ | $R^2$ | Y |
|---|---|---|---|---|---|
| Cl | Cl | H | pyrazol-1-yl (-N(-N=CH-CH=CH-)) | H | N |
| Cl | Cl | H | quinolin-2-yl | H | N |
| Cl | Cl | Cl | -C(CH$_3$)$_3$ | CH$_3$ | N |
| Cl | Br | Br | -C(CH$_3$)$_3$ | CH$_3$ | N |
| Cl | Cl | Cl | -C(CH$_3$)$_2$-CH(CH$_3$)$_2$ | H | N |
| Cl | Br | Br | -C(CH$_3$)$_2$-CH(CH$_3$)$_2$ | H | N |
| Cl | Cl | Cl | 1-methylcyclohexyl | H | N |
| Cl | Cl | Cl | -C(CH$_3$)$_2$-phenyl | H | N |
| Cl | Cl | Cl | -C(CH$_2$F)(CH$_3$)(CH$_2$F) | H | N |

If 4,4-dimethyl-3-hydroxy-3-[(1,2,4-triazol-1-yl)-methyl]-pent-1-ine is used as the starting substance and chlorine gas is used as the reaction component, the course of process (a) according to the invention can be illustrated by the following equation:

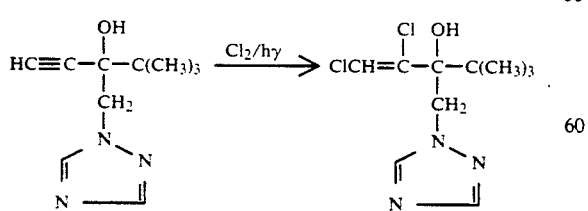

If 1,2-dichloro-3-hydroxy-3-chloromethyl-4,4-dimethyl-pent-1-ene and 1,2,4-triazole are used as starting substances, the course of process (b) according to the invention can be illustrated by the following equation:

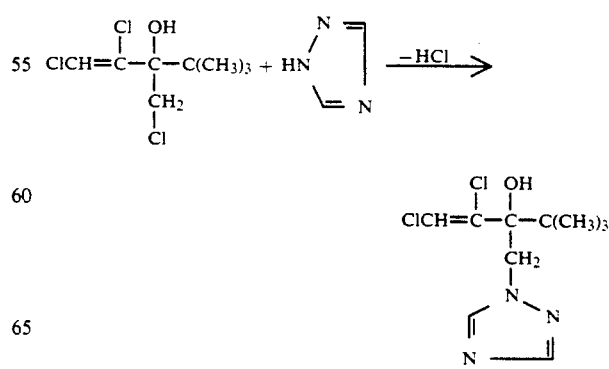

If 4,4-dimethyl-3-hydroxy-3-[(1,2,4-triazol-1-yl)-methyl]-pent-1-ine is used as the starting substance and sodium hypochlorite as well as bromine are used as reaction components, the course of process (c) according to the invention can be illustrated by the following equation:

$$HC\equiv C-\underset{\underset{\underset{N\diagdown N}{\underset{\parallel}{CH_2}}}{\overset{OH}{|}}}{C}-C(CH_3)_3 \xrightarrow{NaOCl}$$

$$Cl-C\equiv C-\underset{\underset{\underset{N\diagdown N}{\underset{\parallel}{CH_2}}}{\overset{OH}{|}}}{C}-C(CH_3)_3 \xrightarrow{Br_2} \underset{Cl}{\overset{Br}{\diagdown}}C=C\underset{\underset{\underset{N\diagdown N}{\underset{\parallel}{CH_2}}}{\overset{Br}{\diagup}}}{\overset{OH}{\underset{|}{-C-C(CH_3)_3}}}$$

Formula (II) provides a general definition of the alkines required as starting substances in carrying out process (a) according to the invention. In this formula, $R^1$, $R^2$ and Y preferably have those meanings which have already been mentioned as preferred for these radicals in connection with the description of the substances of the formula (I) according to the invention.

The alkines of the formula (II) have not previously been disclosed. They can be prepared by a process in which d) azolyl-methyl-ketones of the formula $$R^1-\underset{\underset{O}{\parallel}}{C}-CH_2-N\diagup\diagdown_{N}^{Y} \quad \text{(VII)}$$

in which $R^1$ and Y have the abovementioned meaning, are reacted with acetylene salts of the formula $$HC\equiv CMe \quad \text{(VIII)}$$

in which Me represents an equivalent of a metal cation, in the presence of a diluent, and if appropriate the alkines formed in this reaction of the formula $$HC\equiv C-\underset{\underset{\underset{N\diagdown N}{\underset{\parallel}{CH_2}}}{\underset{|}{R^1}}}{\underset{|}{C}}-R^1 \quad \text{(IIa)}$$

in which $R^1$ and Y have the abovementioned meaning, are reacted with strong bases in the presence of a diluent, and the alcoholates formed in this reaction of the formula $$HC\equiv C-\underset{\underset{\underset{N\diagdown N}{\underset{\parallel}{CH_2}}}{\underset{|}{R^1}}}{\underset{|}{C}}-R^1 \quad \text{(IIb)}$$

in which
$R^1$ and Y have the abovementioned meaning and
$R^3$ represents a cationic radical of a base,
are reacted with halogen compounds of the formula $$R^4-Hal \quad \text{(IX)}$$

in which
$R^4$ represents alkyl, alkenyl, acyl or aralkyl and
Hal represents chlorine, bromine or iodine,
in the presence of a diluent, or e) chloromethyl ketones of the formula $$R^1-\underset{\underset{O}{\parallel}}{C}-CH_2Cl \quad \text{(X)}$$

in which $R^1$ has the abovementioned meaning, are reacted with acetylenes of the formula $$HC\equiv CR^5 \quad \text{(XI)}$$

in which $R^5$ represents hydrogen or an equivalent of a metal cation, if appropriate in the presence of a base and in the presence of a diluent, and the hydroxyalkines formed in this reaction, of the formula $$HC\equiv C-\underset{\underset{CH_2Cl}{|}}{\underset{|}{C}}-R^1 \quad \text{(XII)}$$

in which $R^1$ has the abovementioned meaning, are then reacted with azoles of the formula $$\underset{N\underline{\phantom{--}}}{\overset{H}{\underset{|}{N\diagdown}}}\diagup^{Y} \quad \text{(IV)}$$

in which Y has the abovementioned meaning, in the presence of an acid-binding agent and in the presence of a diluent, and if appropriate the alkines formed in this reaction of the formula $$HC\equiv C-\underset{\underset{\underset{N\diagdown N}{\underset{\parallel}{CH_2}}}{\underset{|}{R^1}}}{\underset{|}{C}}-R^1 \quad \text{(IIa)}$$

in which $R^1$ and Y have the abovementioned meaning, are further reacted in accordance with process (d).

Formula (VII) provides a general definition of the azolyl-methyl ketones required as starting substances in carrying out process (d). In this formula, Y and R¹ preferably have those meanings which have already been mentioned as preferred for these radicals in connection with the description of the substances of the formula (I) according to the invention.

The azolyl-methyl ketones of the formula (VII) are known or can be prepared in a simple manner by processes which are known in principle (compare DE-OS (German Published Specification) 2,431,407).

Formula (VII) provides a general definition of the acetylene salts required as reaction components in process (d). In this formula, Me preferably represents a lithium cation or one equivalent of a cerium(III) cation.

The acetylene salts of the formula (VIII) are known (compare Houben-Weyl, "Methoden der Organischen Chemie (Methods of Organic Chemistry)", Volume V/2a, pages 509 et seq., Georg Thieme Verlag, Stuttgart 1977 and Tetrahedron Letters 25, (1984) 4233).

Diluents which can be used for carrying out the first stage of process (d) are all the inert organic solvents customary for such reactions. Preferred possible solvents are ethers, such as tetrahydrofuran or diethyl ether, and in addition hydrocarbons, such as n-hexane.

The reaction temperatures can be varied within a substantial range in carrying out the first stage of process (d). The reaction is in general carried out at temperatures between −78° C. and +30° C., preferably at temperatures between −70° C. and +20° C.

In carrying out process (d), as when carrying out processes (a), (b), (c) and (e), normal pressure is in general applied.

In carrying out the first stage of process (d), a procedure is in general followed in which first the acetylene salts are prepared and these are then reacted, without prior isolation, with an equivalent amount or an excess or less than the equivalent amount of azolyl-methyl ketone of the formula (VII). Working up is carried out by customary methods. In general, a procedure is followed in which an aqueous salt solution, for example ammonium chloride solution, is first added to the reaction mixture, the reaction mixture is then extracted several times with an organic solvent of low water-solubility and the combined organic phases are dried under reduced pressure and concentrated.

In carrying out the second stage of process (d), the conversion of the alkines of the formula (IIa) into the corresponding alcoholates is carried out by reaction with suitable strong bases, such as alkali metal amides or hydrides, quaternary ammonium hydroxides or phosphonium hydroxides, in an inert diluent, such as, for example, dioxane, at room temperature. Accordingly, R³ in the compounds of the formula (IIb) preferably represents an alkali metal cation, such as a sodium or potassium cation, or a quaternary ammonium or phosphonium cation.

Formula (IX) provides a general definition of the halogen compounds required as reaction components in carrying out the third stage of process (d). In this formula, R⁴ preferably represents the meanings which have already been mentioned for the substituent R² in connection with the description of the substances of the formula (I) according to the invention, with the exception of the meaning of hydrogen. Hal represents chlorine, bromine or iodine.

The halogen compounds of the formula (IX) are known or can be prepared by methods which are known in principle.

Possible diluents in carrying out the second and third stage of process (d) are inert organic solvents. Solvents which can preferably be used are ethers, such as diethyl ether or dioxane; aromatic hydrocarbons, such as benzene, and in individual cases also chlorinated hydrocarbons, such as chloroform, methylene chloride or carbon tetrachloride, as well as hexamethylphosphoric triamide.

The reaction temperatures can be varied within a substantial range in carrying out the second and third stage of process (d). The reaction is in general carried out at temperatures between 0° C. and 120° C., preferably between 20° C. and 100° C.

In carrying out the second stage of process (d), alkines of the formula (IIa) are first reacted with strong bases to give the corresponding alcoholates of the formula (IIb). In the subsequent third stage, 1 to 2 mol of halogen compound of the formula (IX) are preferably employed per mole of an alcoholate of the formula (IIb). To isolate the end products, the reaction mixture is freed from the solvent, and water and an organic solvent are added to the residue. The organic phase is separated off, worked up in the customary manner and purified.

In a preferred embodiment, the procedure in the second and third stage of process (d) is advantageously such that a hydroxy compound of the formula (IIa) is used as the starting substance, the latter is converted into the alkali metal alcoholate in a suitable organic solvent by means of an alkali metal hydride or alkali metal amide, and the product is immediately reacted, without being isolated, with a halogen compound of the formula (IX), alkali metal halide being eliminated to give the compounds of the formula (II) in one operation.

According to another preferred embodiment, the preparation of the alcoholates and the reaction with a halogen compound of the formula (IX) are advantageously carried out in a two-phase system, such as, for example, aqueous sodium hydroxide solution or potassium hydroxide solution/toluene or methylene chloride, with the addition of 0.01–1 mol of a phase transfer catalyst, such as, for example, ammonium compounds or phosphonium compounds, the alcoholates being reacted in the organic phase in the organic phase or at the interface with the halides contained.

Formula (X) provides a general definition of the chloromethyl ketones required as starting substances in carrying out process (e). In this formula, R¹ preferably has those meanings which have already been mentioned as preferred for this radical in connection with the description of the substances of the formula (I) according to the invention.

The chloromethyl ketones of the formula (X) are known or can be prepared by methods which are known in principle (compare DE-OS (German Published Specification) 3,049,461).

Formula (XI) provides a general definition of the acetylenes required as reaction components in process (e). In this formula, R⁵ preferably represents hydrogen, a lithium cation or one equivalent of a magnesium or cerium(III) cation.

The acetylenes of the formula (XI) are known.

Possible bases in carrying out the first stage of process (e) are all the strong bases which are customary for such reactions. Bases which can preferably be used are alkali metal hydroxides, such as potassium hydroxide.

All the inert organic solvents customary for such reactions can be used as diluents in carrying out the first stage of process (e). Preferred possible solvents are ethers, such as tetrahydrofuran or diethyl ether.

The reaction temperatures can be varied within a substantial range in carrying out the first stage of process (e). The reaction is in general carried out at temperatures between −78° C. and +50° C., preferably between −78° C. and +40° C.

In carrying out the first stage of process (e), a procedure is in general followed in which chloromethyl ketones of the formula (X) and acetylenes of the formula (XI) are reacted in approximately equivalent amounts. However, it is also possible to use one or the other of the components in excess. Working up is carried out by customary methods. The hydroxyalkines of the formula (XII) can be further reacted directly with azoles of the formula (IV). However, they can also first be converted into oxiranes and these can then be reacted with azoles of the formula (IV).

In carrying out the second stage of process (e), possible acid-binding agents are all the customary acid acceptors. Acid acceptors which can preferably be used are alkali metal carbonates and bicarbonates, such as sodium carbonate, potassium carbonate or sodium bicarbonate, and furthermore tertiary aliphatic or aromatic amines, such as triethylamine, N,N-dimethylcyclohexyl-amine, N,N-dimethyl-benzylamine and pyridine, and also cyclic amines, such as 1,5-diaza-bicyclo[4.3.0]non-5-ene (DBN), 1,8-diaza-bicyclo[5.4.0]undec-7-ene (DBU) and 1,4-diaza-bicyclo[2.2.2]octane (DABCO).

Possible diluents in carrying out the second stage of process (e) are all the inert organic solvents. Solvents which can preferably be used are aliphatic and aromatic optionally halogenated hydrocarbons, such as pentane, hexane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as dimethyl ether, dibutyl ether, tert.-butyl methyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl and ethyl acetate, nitriles, such as, for example, acetonitrile and propionitrile, and pyridine.

The reaction temperatures can also be varied within a substantial range in carrying out the second stage of process (e). The reaction is in general carried out at temperatures between 0° C. and 200° C., preferably between 20° C. and 150° C.

In carrying out the second stage of process (e), a procedure is in general followed in which an equivalent amount or even an excess of azole of the formula (IV) and 2 to 3 mol of acid-binding agent are employed per mole of hydroxyalkine of the formula (XII). Working up is carried out by customary methods. Further reaction of the alkines of the formula (IIa) which may be desired is carried out in process (e) in the same manner as in process (d).

Preferred possible halogens as reaction components in carrying out process (a) according to the invention are fluorine, chlorine, bromine and iodine, and furthermore mixed halogens, such as chlorine(I) fluoride, bromine(I) fluoride, iodine(I) fluoride, bromine(I) chloride, iodine(I) chloride or iodine(I) bromide (see Methodicium Chimicium, F. Korte, Volume 7, page 842 (1976).

Examples of compounds which supply halogen which may be used are sulphuryl chloride, N-bromosuccinimide with hydrochloric acid, N-chlorosuccinimide with hydrobromic acid or N-chlorosuccinimide with hydrofluoric acid/pyridine (see Synthesis 1973, 780).

The addition of the halogens onto the alkines of the formula (II) can be promoted by the action of light, by heat, by substances which form free radicals, such as organic peroxides, or by surface-active substances, such as charcoal, or metal salts, such as copper(II) chloride or iron(III) chloride. The isomer ratio (E/Z) can in some cases be influenced in this way (see Houben-Weyl, Methoden der Org. Chemie (Methods of Organic Chemistry), Volume V/3, page 551 (1962)).

Diluents which can be used in carrying out process (a) according to the invention are all the inert organic solvents customary for such reactions. Solvents which can preferably be used are halogenated aliphatic hydrocarbons, such as methylene chloride, chloroform and carbon tetrachloride.

The temperatures can be varied within a certain range in carrying out process (a) according to the invention. In general, the reaction is carried out at temperatures between −10° C. and +120° C., preferably between −5° C. and +80° C.

In carrying out process (a) according to the invention, in general an equivalent amount or an excess of halogen or halogen-supplying compound is employed per mole of alkine of the formula (II). Working up is carried out by customary methods. In general, a procedure is followed in which the mixture is diluted with an organic solvent of low water-solubility, washed with water, and the organic phase is dried and concentrated. However, it is also possible for the reaction mixture to be concentrated directly, when the reaction has ended, by stripping off the volatile components under reduced pressure. If appropriate, the products formed can be further purified by customary methods.

Formula (III) provides a general definition of the alkenes required as starting substances in process (b) according to the invention. In this formula, $R^1$, $R^2$, $X^1$ and $X^2$ preferably have those meanings which, in connection with the description of the substances of the formula (I) according to the invention, have already been mentioned as preferred for these substances. Z preferably represents chlorine, bromine, iodine, methylsulphonate or p-tolylsulphonate.

The alkenes of the formula (III) can be prepared by customary methods. Thus, for example, alkenes of the formula (III) are obtained by reacting hydroxyalkines of the formula (XII) with halogens in the presence of a diluent. The reaction conditions used correspond to those used in the case of process (a) according to the invention.

Possible diluents in carrying out process (b) according to the invention are all the customary inert organic solvents. Those solvents which have already been mentioned as preferred solvents in connection with the description of the second stage of process (e) can preferably be used.

Possible acid-binding agents in carrying out process (b) according to the invention are all the customary acid acceptors. All those acid-binding agents which have already been mentioned as preferred acid acceptors in connection with the description of the second stage of process (e) can preferably be used.

The reaction temperatures can be varied within a substantial range in carrying out process (b) according to the invention. The reaction is in general carried out at temperatures between 0° C. and 150° C., preferably between 20° C. and 120° C.

In carrying out process (b) according to the invention, a procedure is in general followed in which an equivalent amount or an excess of azole of the formula (IV) and 2 to 3 mol of acid-binding agent are employed per mole of alkene of the formula (III). Working up is carried out by customary methods.

Formula (V) provides a general definition of the hypohalogenites required as reaction components in carrying out process (c) according to the invention. In this formula, M preferably represents a sodium or potassium ion, and $X^4$ preferably represents chlorine, bromine and iodine.

Possible diluents in carrying out the first stage as well as the second stage of process (c) according to the invention are all inert organic solvents which are customarily used for reactions of this type. Solvents which can preferably be used are halogenated aliphatic hydrocarbons, such as methylene chloride, chloroform and carbon tetrachloride.

The reaction temperatures can be varied within a certain range in carrying out the first stage as well as the second stage of process (c) according to the invention. In general, the reaction is carried out at temperatures between $-10°$ C. and $+120°$ C., preferably between $-5°$ C. and $+80°$ C.

In carrying out the first stage of process (c) according to the invention, in general an excess of hypohalogenite is employed per mole of alkine of the formula (II).

In carrying out the second stage of process (c) according to the invention, in general an equivalent amount or an excess of halogen or halogen-supplying compound is employed per mole of halogeno-alkine of the formula (VI). In carrying out the first stage as well as the second stage, working up is carried out by customary methods.

The halogenovinyl-azole derivatives of the formula (I) obtainable by the processes according to the invention can be converted into acid addition salts or metal salt complexes.

Those acids which have already been mentioned as preferred acids in connection with the description of the acid addition salts according to the invention are preferably suitable for the preparation of acid addition salts of the compounds of the formula (I).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Those salts of metals which have already been mentioned as preferred metal salts in connection with the description of the metal salt complexes according to the invention are preferably suitable for the preparation of metal salt complexes of the compounds of the formula (I).

The metal salt complexes of the compounds of the formula (I) can be obtained in a simple manner by customary processes, such as, for example, by dissolving the metal salt in alcohol, for example ethanol, and adding the solution to compounds of the formula (I). The metal salt complexes can be isolated in a known manner, for example by filtration, and, if appropriate, purified by recrystallization.

The active compounds according to the invention have potent microbicidal action and can be used as fungicides in plant protection and in the preservation of materials.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:

Xanthomonas species, such as, for example, *Xanthomonas oryzae*; Pseudomonas species, such as, for example, *Pseudomonas lachrymans*; Erwinia species, such as, for example, *Erwinia amylovora*; Pythium species, such as, for example, *Pythium ultimum*; Phytophthora species, such as, for example, *Phytophthora infestans*; Pseudoperonospora species, such as, for example, *Pseudoperonospora humuli* or *Pseudoperonospora cubensis*; Plasmopara species, such as, for example, *Plasmopara viticola*; Peronospora species, such as, for example, *Peronospora pisi* or *P. brassicae*; Erysiphe species, such as, for example, *Erysiphe graminis*; Sphaerotheca species, such as, for example, *Sphaerotheca fuliginea*; Podosphaera species, such as, for example, *Podosphaera leucotricha*; Venturia species, such as, for example, *Venturia inaequalis*; Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus*; Puccinia species, such as, for example, *Puccinia recondita*; Tilletia species, such as, for example, *Tilletia caries*; Ustilago species, such as, for example, *Ustilago nuda* or *Ustilage avenae*; Pellicularia species, such as, for example, *Pellicularia sasakii*; Pyricularia species, such as, for example, *Pyricularia oryzae*; Fusarium species, such as, for example, *Fusarium culmorum*; Botrytis species, such as, for example, *Botrytis cinerea*; Septoria species, such as, for example, *Septoria nodorum*; Leptosphaeria species, such as, for example, *Leptosphaeria nodorum*; Cercospora species, such as, for example, *Cercospora canescens*; Alternaria species, such as, for example, *Alternaria brassicae* and Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal and rice diseases, such as Pseudocercosporella, Erysiphe, Fusarium, Pyrenophora, Cochliobolus, Pyricularia and Pellicularia, and for combating cucumber mildew and apple scab, and also for combating Botrytis in fruit, wine and vegetable growing.

In the preservation of materials, the compounds according to the invention can be used to preserve industrial materials against attack or destruction by undesired microorganisms. Industrial materials in this connection are to be understood as non-living materials which have been prepared for use in industry. Industrial materials which are to be protected from microbial change or destruction by the active compounds according to the invention can be, for example, adhesives, sizes, paper, card, textiles, leather, wood, paints, articles made of plastic, cooling lubricants and other materials which can be attacked or decomposed by microorganisms. In the context of the materials to be preserved, components of production lines, for example cooling water circulations, which can be impaired by multiplication of microorganisms may also be mentioned. Industrial materials which may be mentioned as preferred in the context of the present invention are adhesives, sizes, paper and card, leather, wood, paints, cooling lubricants and cooling circulations, particularly preferably wood.

Examples which may be mentioned of microorganisms which can cause degradation to or a change in the industrial materials are bacteria, fungi, yeasts, algae and slime organisms. The active compounds according to the invention preferentially act against fungi, in particular moulds, fungi which discolour and destroy wood (Basidiomycetes), and against slime organisms and algae.

Microorganisms of the following genera may be mentioned as examples: Alternaria, such as *Alternaria tenuis*, Aspergillus, such as *Aspergillus niger*, Chaetomium, such as *Chaetomium globosum*, Coniophora, such as *Coniophora puteana*, Lentinus, such as *Lentinus tigrinus*, Penicillium, such as *Penicillium glaucum*, Polyporus, such as *Polyporus versicolor*, Aureobasidium such as *Aureobasidium pullulans*, Sclerophoma, such as *Sclerophoma pityophila*, Trichoderma, such as *Trichoderma viride*, Escherichia, such as *Escherichia coli*, Pseudomonas, such as *Pseudomonas aeruginosa* and Staphylococcus, such as *Staphylococcus aureus*.

The substances according to the invention moreover also have plant growth-regulating properties.

Depending on their particular physical and/or chemical properties, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

The formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

If applied in plant protection, the formulations in general contain between 0.1 and 95 per cent by weight of active compound, preferably between 0.5 and 90%.

If applied in plant protection, the active compounds according to the invention can be present in the formulations as a mixture with other known active compounds, such as fungicides, insecticides, acaricides and herbicides, and in mixtures with fertilizers and growth regulators.

If applied in plant protection, the active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

Microbicidal agents in general contain the active compounds in an amount of 1 to 95% by weight, preferably 10 to 75% by weight.

In the preservation of materials, the use concentrations of the active compounds according to the invention depend on the nature and occurrence of the microorganisms to be combated and on the composition of the material to be preserved. The optimum amount to be used can be determined by test series. The use concentrations are in general in the range from 0.001 to 5% by weight, preferably 0.05 to 1.0% by weight, based on the material to be preserved.

In the preservation of materials, the active compounds according to the invention can also be used in mixture with other known active compounds. The following active compounds may be mentioned as examples: benzyl alcohol mono(poly)hemiformal and other compounds which split off formaldehyde, benzimidazolyl methylcarbamates, tetramethylthiuram disulphide, zinc salts of dialkyldithiocarbamates, 2,4,5,6-tetrachloroisophthalonitrile, thiazolylbenzimidazole, mercaptobenzothiazole, organotin compounds, methylene bisthiocyanate, 2-thiocyanatomethylthiobenzothiazole, phenol derivatives, such as 2-phenylphenol, (2,2'-dihydroxy-5,5'-dichloro)diphenylmethane and 3-methyl-4-chlorophenol, N-trihalogenomethylthio compounds, such as folpet, fluorofolpet, dichlofluanid.

The preparation and use of the active compounds according to the invention are illustrated by the following examples.

PREPARATION EXAMPLES

Example 1

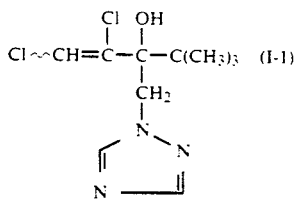

(B)

A stream of chlorine gas is passed into a solution of 3.86 g (20 mmol) of 4,4-dimethyl-3-hydroxy-3-[(1,2,4-triazol-1-yl)methyl]-1-pentine in 20 ml of absolute methylene chloride at 0° to 5° C. over a period of 6 hours, while irradiating with a 500 watt lamp. The reaction mixture is subsequently stirred at room temperature for 15 hours and then diluted with methylene chloride and extracted by shaking with water. The organic phase is dried and then concentrated under reduced pressure by stripping off the solvent. 4.7 g (89% of theory) of 1,2-dichloro-4,4-dimethyl-3-hydroxy-3-[(1,2,4-triazol-1-yl)-methyl]-1-pentene are obtained in the form of a solid substance of melting point 49°–52° C. This substance is a mixture of isomers A:B=1:50.

NMR (CDCl$_3$): (B) δ1.15 (s, 9H) 4.3 (d, J=14 Hz, 1H), 5.0 (d, J=14 Hz, 1H), 6.68 (s, 1H), 7.95 (s, 1H), 8.25 (s, 1H)

Preparation of the Starting Substance

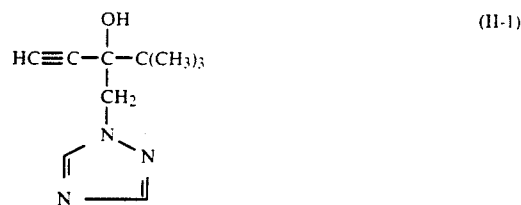

13 g (0.5 mol) of acetylene are passed into 880 ml of absolute tetrahydrofuran at −70° C. and metalated by dropwise addition of 200 ml (0.5 mol) of butyllithium in hexane. After 30 minutes, a solution of 78.5 g (0.47 mol) of 3,3-dimethyl-1-(1,2,4-triazol-1-yl)-2-butanone in 150 ml of absolute tetrahydrofuran is added dropwise at −70° C. The reaction mixture is subsequently stirred at −70° C. for 2 hours and then thawed and stirred at 20° C. for a further 2 hours. After dilution with saturated aqueous ammonium chloride solution, the mixture is extracted several times by shaking with methylene chloride. The combined organic phases are dried and then concentrated under reduced pressure. 74 g of a product which, according to analysis by gas chromatography, consists of 38% of 3,3-dimethyl-1-(1,2,4-triazol-1-yl)-2-butanone and of 57% of 4,4-dimethyl-3-hydroxy-3-[(1,2,4-triazol-1-yl)methyl]-1-pentine remain. After recrystallization from toluene, pure 4,4-dimethyl-3-hydroxy-[(1,2,4-triazol-1-yl)-methyl]-1-pentine of melting point 129°–131° C. is obtained.

NMR (CDCl$_3$): δ1.2 (s, 9H), 2.35 (s, 1H), 3.75 (OH), 4.4 (AB, 2H), 8.0 (s, 1H), 8.25 (s, 1H).

Example 2

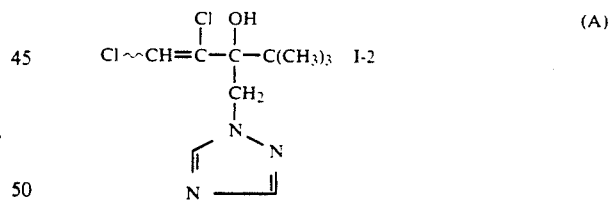

(A)

25 g of charcoal are initially introduced in granule form into 100 ml of absolute methylene chloride at 0°–5° C. 6.3 g (88 mmol) of chlorine gas are then passed in, 9.65 g (50 mmol) of 4,4-dimethyl-3-hydroxy-3-[(1,2,4-triazol-1-yl)-methyl]-1-pentine in 100 ml of absolute methylene chloride are then added dropwise and the mixture is subsequently stirred at room temperature for 13 hours. After filtering and stripping off the solvent, 3.2 g of 1,2-dichloro-4,4-dimethyl-3-hydroxy-3-[(1,2,4-triazol-1-yl)-methyl]-1-pentane remain as a mixture of isomers A:B=25:1 of melting point 59°–62° C.

NMR (CDCl$_3$): δ1.2 (s, 9H), 2.85 (OH), 4.3 (broad t, 1H), 5.0 (broad t, 1H), 6.35 (s, 1H), 8.05 (s, 1H), 8.4 (broad s, 1H)

Example 3

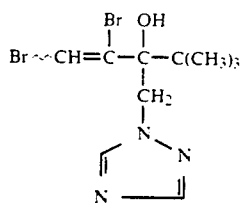 (I-3)

A solution of 6.4 g (40 mmol) of bromine in 20 ml of methylene chloride is added dropwise to a solution of 3.86 g (20 mmol) of 4,4-dimethyl-3-hydroxy-3-[(1,2,4-triazol-1-yl)-methyl]-1-pentine in 30 ml of absolute methylene chloride at 0° to 5° C., while stirring. The reaction mixture is subsequently stirred at 20° C. for 5 hours and then concentrated by stripping off volatile constituents under reduced pressure. 5.7 g (81% of theory) of 1,2-dibromo-4,4-dimethyl-3-hydroxy-3-[(1,2,4-triazol-1-yl)-methyl]-1-pentene are obtained in this manner in the form of an oil. This substance is a mixture of isomers A:B=1:25.

NMR (CDCl$_3$): (B) δ1.25 (s, 9H), 4.4 (d, J=15 Hz, 1H), 5.1 (d, J=15 Hz, 1H), 6.7 (s, 1H), 8.2 (s, 1H), 8.9 (s, 1H).

EXAMPLE 4

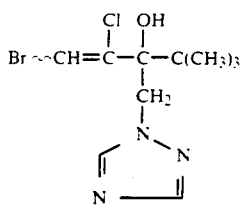 (I-4)

Hydrogen chloride gas is passed into a solution of 1.93 g (10 mmol) of 4,4-dimethyl-3-hydroxy-3-[(1,2,4-triazol-1-yl)-methyl]-1-pentine in 30 ml of methylene chloride at −20° C. until saturation is reached. 1.8 g (20 mmol) of N-bromosuccinimide are then added in portions and the mixture is subsequently stirred at 0° C. for 1 hour and at room temperature for 12 hours. HCl and solvent are stripped off in vacuo and the residue is worked up with methylene chloride and dilute sodium hydroxide solution. 2.1 g (68% of theory) of 1-bromo-2-chloro-4,4-dimethyl-3-hydroxy-3-((1,2,4-triazol-1-yl)-methyl]-1-pentene are thus obtained as a mixture of isomers of melting point 45°-48° C.

The compounds listed in the following table 2 are also prepared by the methods described in Examples 1 to 4:

TABLE 2

$$X^1-CH=C(X^2)-C(OR^2)(R^1)-CH_2-N\text{(triazolyl-Y)} \quad (Ia)$$

| Example No. | Compound No. | $X^1$ | $X^2$ | $R^1$ | $R^2$ | Y | Melting point (°C.) |
|---|---|---|---|---|---|---|---|
| 5 | I-5 | Cl | Cl | 2,4-dichlorophenyl | H | N | 151-152 (Isomeric mixture) |
| 6 | I-6 | Br | Br | 2,4-dichlorophenyl | H | N | 95 (decomposition) (Isomeric mixture) |
| 7 | I-7 | Br | Br | 4-chlorophenyl | H | N | 118-122 (Isomeric mixture) |
| 8 | I-8 | Cl | Cl | 4-chlorophenyl | H | N | 135-160 (Isomeric mixture) |
| 9 | I-9 | Cl | Cl | —C(CH$_3$)$_3$ | CH$_3$ | N | Oil |
| 10 | I-10 | Cl | Cl | —C(CH$_3$)$_3$ | COCH$_3$ | N | 87-92 |
| 11 | I-11 | Cl | Cl | —C(CH$_3$)$_2$-(4-chlorophenyl) | H | N | Oil |

TABLE 2-continued

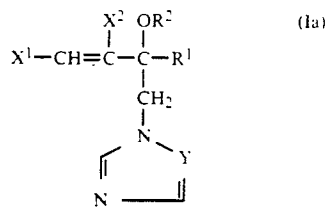

| Example No. | Compound No. | X¹ | X² | R¹ | R² | Y | Melting point (°C.) |
|---|---|---|---|---|---|---|---|
| 12 | I-12 | Cl | Cl | —C(CH₃)₂—CH₂Cl | H | N | Oil |
| 13 | I-13 | Br | Br | —C₆H₄—Cl (4-chlorophenyl) | H | CH | Oil |
| 14 | I-14 | Br | Br | —C(CH₃)₂—CH(Br)—CH₂Br | H | N | Oil |
| 15 | I-15 | Br | Br | 2-chlorocyclopropyl | H | N | 154–158 |
| 16 | I-16 | Cl | Cl | —C(CH₃)₃ | H | N | 53–56 (Isomeric mixture) |

EXAMPLE 17

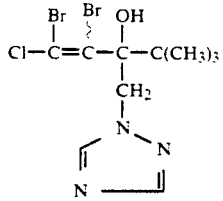   (I-17)

9.65 (50 mmol) of 4,4-dimethyl-3-hydroxy-3-[(1,2,4-triazol-1-yl)-methyl]-1-pentine in 20 ml of methylene chloride are stirred for 3 days with 400 ml (150 mmol) of a solution of sodium hypochlorite at room temperature. The reaction mixture is then extracted by shaking with methylene chloride. After drying the organic phase and stripping off the solvent in vacuo, there are obtained 9.8 g (43 mmol; 86% of theory) of 1-chloro-4,4-dimethyl-3-hydroxy-3-[(1,2,4-triazol-1-yl)-methyl]-1-pentine having a melting point of 88° C.

NMR (CDCl₃): δ1.15 (s, 3H), 4.4 (s, 2H) 8.0 (s, 1H), 8.3 (s, 1H)

1.6 g of bromine dissolved in 10 ml of absolute methylene chloride are added dropwise to a solution of 2,3 g (10 mmol) of 1-chloro-4,4-dimethyl-3-hydroxy-3-[(1,2,4-triazol-1-yl)-methyl]-1-pentine in 20 ml of absolute methylene chloride at 20° C. The reaction mixture is subsequently stirred for 5 hours at room temperature and then the solvent is stripped off under reduced pressure. 3.8 g (100% of theory) of 1-chloro-1,2-dibromo-4,4-dimethyl-3-hydroxy-3-[(1,2,4-triazol-1-yl)-methyl]-1-pentene are obtained in the form of a solid substance of melting point 78°–81° C. This substance is a mixture of isomers A:B=1:3,6

NMR (CDCl₃): A) δ1.25 (s, 9H), 4.4 (d, J=14 Hz, 1H) 5.25 (d, J=14 Hz, 1H), 5.6 (OH), 8.1 (s, 1H), 8.7 (s, 1H). B) δ1.25 (s, 9H), 4.6 (d, J=14 Hz, 1H) 5.2 (d, J=14 Hz, 1H), 5.6 (OH), 8.1 (s, 1H), 8.9 (s, 1H).

The compounds listed in the following table 3 are also prepared by the method described in Example 17.

TABLE 3

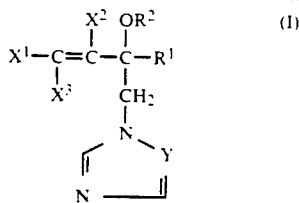

| Example No. | Compound No. | $X^1$ | $X^2$ | $X^3$ | $R^1$ | $R^2$ | Y | Melting point (°C.) |
|---|---|---|---|---|---|---|---|---|
| 18 | I-18 | Cl | Cl | Cl | —C(CH$_3$)$_3$ | H | N | Oil |
| 19 | I-19 | Cl | Cl | Cl | —C$_6$H$_4$—Cl | H | N | 63–65 |
| 20 | I-20 | Cl | Cl | Cl | cyclopropyl-Cl | H | N | Oil |

USE EXAMPLES

EXAMPLE A

Pyricularia Test (Rice)/Protective

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, substances (I-1) and (I-3) according to the invention exhibit a very good activity.

EXAMPLE B

Pellicularia Test (Rice)

Solvent: 12.5 parts by weight of acetone
Emulsifier: 0.3 part by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, substances (I-1) and (I-5) according to the invention exhibit a very good activity.

EXAMPLE C

Botrytis Test (Beans)/Protective

Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humid chamber at 20° C. 3 days after the inoculation, the size of the infected spots on the leaves is evaluated.

In this test, substance (I-1) according to the invention exhibits a very good activity.

EXAMPLE D

Erysiphe Test (Barley)/Protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, substances (I-1) and (I-3) according to the invention exhibit a very good activity.

EXAMPLE E

*Leptosphaeria nodorum* Test (Wheat)/Protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a spore suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, substances (I-1) and (I-3) according to the invention exhibit a very good activity.

EXAMPLE F

*Pseudocercosporella herpotrichoides* Test (Wheat)/Protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dew-moist. After the spray coating has dried on, the plants are inoculated at the base of the stem with spores of *Pseudocercosporlla herpotrichoides*.

The plants are then placed in a greenhouse at a temperature of about 10° C. and a relative atmospheric humidity of about 80%.

Evaluation is carried out 21 days after the inoculation.

In this test, substance (I-5) according to the invention exhibits a very good activity.

The compounds shown below were employed as comparison substances in the following use examples.

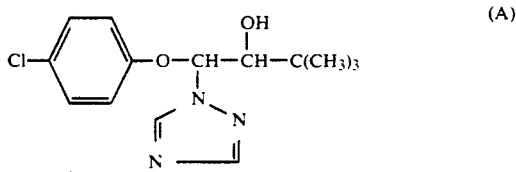

(A)

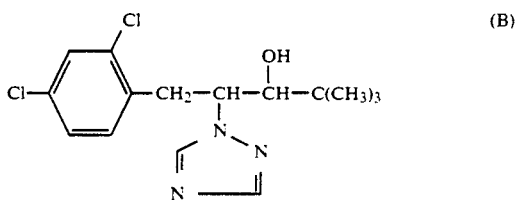

(B)

EXAMPLE G

To demonstrate the activity against fungi, the minimum inhibitory concentrations (MIC) of active compounds according to the invention are determined.

Active compounds according to the invention are added in concentrations of 0.1 mg/l to 5,000 mg/l to an agar prepared from beer wort and peptone. After the agar has solidified, it is contaminated with pure cultures of the test organisms listed in the table. After storage at 28° C. and 60 to 70% relative atmospheric humidity for 2 weeks, the MIC is determined. The MIC is the lowest concentration of active compound at which there is no growth at all of the species of microbe used; it is listed in the following table G.

TABLE G

| Test organisms | MIC's [mg/l] for the action of substances on fungi |||||| ||
|---|---|---|---|---|---|---|---|---|
| | Compounds according to the invention |||||| Comparison substances ||
| | I-3 | I-1 | I-16 | I-17 | I-18 | I-12 | (A) | (B) |
| *Alternaria tenius* | 35 | 50 | 35 | 500 | 100 | 20 | >1000 | >5000 |
| *Aspergillus niger* | 75 | 7.5 | 7.5 | 50 | <20 | 5 | >5000 | 5000 |
| *Aureobasidium-pullulans* | 35 | 5 | 7.5 | 50 | 10 | 5 | 1000 | >5000 |
| *Chaetomium globosum* | 100 | 5 | 7.5 | <20 | <20 | 2 | 90 | 5000 |
| *Cladosporium cladosporioides* | 100 | 20 | 50 | 200 | 50 | 20 | 500 | 1000 |
| *Lentinus tigrinus* | 20 | 5 | 5 | 20 | 7.5 | 10 | 750 | 500 |
| *Penicillium glaucum* | 50 | 200 | | 500 | 500 | 200 | 750 | 5000 |
| *Sclerophoma pityophila* | 20 | 0.5 | 1 | 5 | 1 | 0.5 | | |
| *Trichoderma viride* | 200 | 75 | 100 | 500 | 100 | 50 | | |

EXAMPLE H

Determination of the toxic limit values (kg/m$^3$ of wood) of the active compounds according to the invention for *Coniophora puteana* and *Polyporus versicolor* on pine and beech wood.

The toxic limit values are determined in accordance with the method described by H. P. Sutter, Int. Biodeterioration Bulletin 14 (3), 1978, pages 95 to 99.

For the tests, in each case freshly cut, thin pieces of cross-cut wood (size 40×40 mm, thickness about 2 mm) are impregnated with solutions of various concentrations of the active compounds in vacuo, 15 wood samples being impregnated with each solution of a particular concentration of active compound. Of these 15 samples 5 are in each case used for a mycological test.

The amount of active compound absorbed is determined from the solvent retention (which is determined by weighing the piece of wood before and after the impregnation), the wood density and the concentration of the active compound in the impregnating solution which remains.

Before the mycological test, the test specimens are sterilized with propylene oxide and 1 test specimen each is introduced into a Petri dish in contact with the fully developed mycelium of test fungus on malt extract agar. After 6 weeks at 21° to 23° C., the toxicity limits are ascertained visually.

The toxicity limits (kg/m$^3$ of wood) for substances according to the invention are shown in the following table; the toxicity limits indicate the concentrations at which the wood is still just attacked (lower limit value) and at which the wood is no longer attacked (upper limit value).

TABLE H

| Toxicity limits [kg/m$^3$ of wood] of active compounds according to the invention for wood destructing fungi | | |
|---|---|---|
| Active Compound | Coniphora puteana on pine wood | Polyporus versicolor on beech tree wood |
| I-3 | 0.71–1.42 | 0.21–0.68 |
| I-1 | 0.05–0.26 | <0.02 |

It is understood that the specification and examples are illustrative but not limitative of the present invention and that other embodiments within the spirit and scope of the invention will suggest themselves to those skilled in the art.

What is claimed is:

1. A halogenvinyl-azole derivative of the formula

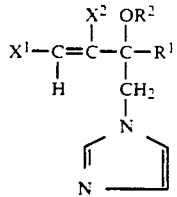

in which

R$^1$ represents phenyl, which can be substituted by one to three identical or different substituents from the group consisting of halogen, alkyl having 1 to 4 carbon atoms, alkoxy having 1 to 4 carbon atoms, alkylthio having 1 to 4 carbon atoms, halogenalkyl having 1 or 2 carbon atoms and 1 to 5 identical or different halogen atoms, halogenalkoxy having 1 or 2 carbon atoms and 1 to 5 identical or different halogen atoms, halogenalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy part, alkoximinoalkyl having 1 to 4 carbon atoms in the alkoxy part and 1 to 4 carbon atoms in the alkyl part, nitro and cyano, R$^2$ represents hydrogen, alkyl having 1 to 6 carbon atoms or alkenyl having 3 to 6 carbon atoms, X$^1$ represents fluorine, chlorine, bromine or iodine and x$^2$ represents fluorine, chlorine, bromine or iodine, or an addition product thereof with an acid or metal salt.

2. A compound or addition product thereof according to claim 1, in which

R$^1$ represents phenyl which can be substituted by one to three identical or different substituents from the group consisting of fluorine, chlorine, bromine, methyl, ethyl, tert.-butyl, methoxy, ethoxy, methylthio, trifluoromethyl, trifluoromethoxy, trifluoromethylthio, chlorodifluoromethoxy, chlorofluoromethylthio, methoxycarbonyl, ethoxycarbonyl, methoximinoethyl, 1-methoximinoethyl, nitro and cyano, and R$^2$ represents hydrogen, methyl, ethyl, n-propyl, isopropyl, n-butyl or allyl.

3. A compound according to claim 1, wherein such compound is 1,2-dibromo-3-hydroxy-3-(4-chlorophenyl)-4-(1,3-imidazolyl)-1-butene of the formula

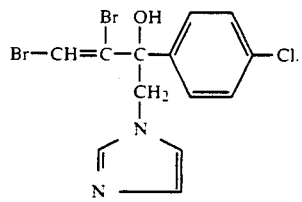

4. A microbicidal composition comprising a microbicidally effective amount of a compound or addition product according to claim 1 and an inert diluent.

5. A method of combating microbes in plant protection and in the preservation of materials, which method comprises applying to such microbes or to their habitat a microbicidally effective amount of a compound or addition product according to claim 1.

6. A method of combating microbes in plant protection and in the preservation of materials, which method comprises applying to such microbes or to their habitat a microbicidally effective amount of a compound or addition product according to claim 3.

* * * * *